United States Patent
Bostrom et al.

(10) Patent No.: US 6,496,254 B2
(45) Date of Patent: Dec. 17, 2002

(54) METHOD AND DEVICE FOR INSPECTING OBJECTS

(75) Inventors: Gunnar Bostrom, Bromma (SE); Hans Ahlen, Stockholm (SE); Mattias Johannesson, Linkoping (SE); Simon Sandgren, Stockholm (SE)

(73) Assignee: Mydata Automation AB, Bromma (SE)

( * ) Notice: Subject to any disclaimer, the term of this patent is extended or adjusted under 35 U.S.C. 154(b) by 0 days.

(21) Appl. No.: 09/906,656

(22) Filed: Jul. 18, 2001

(65) Prior Publication Data

US 2002/0030808 A1 Mar. 14, 2002

Related U.S. Application Data

(63) Continuation of application No. PCT/SE99/02349, filed on Dec. 14, 1999.

(30) Foreign Application Priority Data

Jan. 18, 1999 (SE) .............................................. 9900124

(51) Int. Cl.$^7$ ............................................. G01M 21/00
(52) U.S. Cl. .................................. 356/237.2; 356/237.5
(58) Field of Search ......................... 356/237.1–237.5, 356/239.1–239.3, 614, 625, 628, 635; 250/559.19, 559.21, 559.22, 559.29; 382/144, 145

(56) References Cited

U.S. PATENT DOCUMENTS

| | | | | |
|---|---|---|---|---|
| 4,449,818 A | * | 5/1984 | Yamaguchi et al. | 356/237.1 |
| 4,583,857 A | * | 4/1986 | Grammerstorff et al. | 356/375 |
| 5,032,735 A | * | 7/1991 | Kobayashi et al. | 250/572 |
| 5,048,965 A | * | 9/1991 | Amir | 356/376 |
| 5,134,665 A | | 7/1992 | Jyoko | 356/237.1 |
| 5,162,866 A | | 11/1992 | Tomiya et al. | 356/237.5 |
| 5,302,836 A | * | 4/1994 | Siu | 250/572 |
| 5,686,994 A | * | 11/1997 | Tokura | 356/294 |
| 5,815,274 A | * | 9/1998 | Dlugos | 356/376 |
| 5,835,620 A | * | 11/1998 | Kaplan et al. | 382/133 |
| 5,912,732 A | | 6/1999 | Sekine | 382/8 |
| 6,295,126 B1 | * | 9/2001 | Miyazaki et al. | 356/237.5 |
| 6,344,897 B2 | * | 2/2002 | Miyazaki et al. | 356/237.4 |

FOREIGN PATENT DOCUMENTS

EP    A1898163    2/1999

OTHER PUBLICATIONS

1988 Conference on Precision Electromagnetic Measurements, Tsukuba, Ibaraki, Japan, H. Ikeda: "Surface mounted parts inspection and correction for PC board warpage", pp. 237–238.

* cited by examiner

Primary Examiner—Michael P. Stafira
(74) Attorney, Agent, or Firm—Birch, Stewart, Kolasch & Birch, LLP

(57) ABSTRACT

A method and a device for contactless inspection of objects on a substrate, by means of an inspection device during relative motion between the substrate and the inspection device, wherein the following steps are performed by the method;
generating a first image comprising object height information by illuminating at least a portion of the substrate comprising one or more objects by means of first radiator and imaging at least one of said one or more objects illuminated by said first radiator onto a two-dimensional matrix sensor having a portionwise addressable matrix of pixel elements;
generating a second image comprising object area information by illuminating at least a portion of the substrate comprising one Or more objects by means of second radiator and imaging at least one of said one or more objects illuminated by said second radiator onto said sensor;
extracting the object height information, by means of said sensor, from said first image; and
extracting the object area information, by means of said sensor, from said second image.

35 Claims, 5 Drawing Sheets

METHOD AND DEVICE FOR INSPECTING OBJECTS

This application is a continuation of PCT application No. PCT/SE99/02349, filed Dec. 14, 1999.

BACKGROUND OF THE INVENTION

1. Field of the Invention

The present invention generally relates to a method and device for contactless inspection of objects on a substrate, during relative motion between the substrate and the inspection device.

2. Description of Background Art

When arranging objects on a substrate geometrical and other properties of the objects are important for the performance of the resulting product. Consequently, it is desired to be able to quickly and accurately perform an automatic inspection of these properties. Geometrical properties can for example be volume, position on the substrate, diameter, shape of outline, scratches, surface roughness etc. Other properties can be, colour, etc. An automatic inspection of the properties is difficult to perform at high speed and high accuracy. For example, in the process of applying solder paste to the substrate, by dispensing it or the like, the properties of the resulting solder paste deposit, e.g. volume and position, are important for the subsequent process steps and final yield.

Prior art is generally based on different imaging technologies such as 2-dimensional image processing, pattern recognition and/or 3-dimensional optical triangulation, stereo photography, moiré methods and white-light interferometry.

For obtaining height information of an object, laser triangulation is often used, such as in an apparatus and a method for inspecting solder printing as disclosed in U.S. Pat. No. 5,134,665. A radiation source, generally a laser, is positioned at a lateral distance from a sensor and illuminating the object to be inspected from one direction. The object is imaged onto the sensor via a radiation focusing element, such as refractive optics. The most common triangulation methods employ illumination with a single spot, a sheet-of-light or multistrip-light triangulation. The sensor views the object from another direction than the object is illuminated from and, thus, detects radiation reflected or reemitted from the object. Since the sensor is two-dimensional and since the positions of the radiation source and the sensor and the base plane for the object are known, it is possible to determine the height of the object by determining the direction of the radiation incident on the sensor.

Additionally, by scanning the whole object and determining a large number of height points or height profiles it is possible to determine an approximate volume of the object.

However, there are problems associated with prior art methods and devices. It is desired to combine speed and flexibility in one and the same arrangement. Generally, prior art methods and devices are dedicated to a single task and often they are not fast enough to comply with current and future demands.

In the above mentioned U.S. Pat. No. 5,134,665 there is disclosed an apparatus for inspecting solder paste prints on a printed circuit board (PCB), which is one type of substrate. Other types of substrate are for example substrates for ball grid arrays (BGA), chip scale packages (CSP), quad flat packages (QFP), and flip-chips. The apparatus measures print deviation, film thickness and print pattern of solder paste printed on pads formed on the PCB. A height measurement is performed by means of a laser ray illuminating the PCB pointwise. By mutually moving the apparatus and the PCD the laser point is scanned over a single solder paste object. By scanning the object in orthogonal X- and Y-directions the projection of the object is obtained in the form of an X-direction and a Y-direction profile line showing both the solder paste object and the underlying pad. By this known apparatus the positions and thicknesses of screen printed solder paste objects in relation to pre-printed pads are determinable. Drawbacks of this known apparatus are the limited use thereof. For example, neither accurate volume measurements nor accurate area measurements are performable, at least not reasonably fast, since this would require a vast number of scans in both directions.

Another solution dedicated for inspection of solder paste prints on a PCB is an apparatus manufactured by Philips called TriScan. The TriScan apparatus uses an advanced optical scanning system comprising a 20-side polygonal mirror rotating at a very high speed of up to 50 revolutions per second. A laser ray is projected onto the mirror and thereby a laser point is swept over the object at a rate of up to 1000 light sweeps per second. By advanced sets of mirrors the object is illuminated by said sweeps and reflected light is caught and guided to a sensor. While this apparatus enables several types of properties to be inspected at high speed it is complex and performs only measurements of height profiles as a basis for all determinations. The limitations to height profile measurements causes a limited accuracy. By measuring the profiles extremely closely, a certain improvement of accuracy may be obtained, However, this requires a high speed of measurement, which is difficult to achieve.

SUMMARY OF THE INVENTION

One object of this invention is to provide an inspection device for inspection of objects on a substrate during relative motion between the device and the substrate, and a method for inspection of objects on a substrate by means of such an inspection device, wherein said device and said method in an improved way combine inspection accuracy and a multiple task capability at high speed and low cost.

In one aspect the present invention relates to a method for contactless inspection of objects on a substrate, by means of an inspection device during relative motion between the substrate and the inspection device. The method comprises the steps of:

generating a first image comprising object height information by illuminating at least a portion of the substrate comprising one or more objects by means of first radiation means and imaging at least one of said one or more objects illuminated by said first radiation means onto a two-dimensional matrix sensor means having a portionwise addressable matrix of pixel elements;

generating a second image comprising object area information by illuminating at least a portion of the substrate comprising one or more objects by means of second radiation means and imaging at least one of said one or more objects illuminated by said second radiation means onto said sensor means;

extracting the object height information, by means of said sensor means, from said first image; and extracting the object area information, by means of said sensor means, from said second image.

In another aspect the invention relates to a device for performing the above method. The device comprises a two-dimensional matrix sensor means having a portionwise addressable matrix of pixel elements; a first radiation means; a second radiation means; and imaging means for imaging radiation originating from an object plane onto the sensor means. Said first radiation means is arranged for illuminating at least a portion of the substrate comprising one or more objects, when the substrate is in said object plane, said imaging means thereby generating a first image of at least one of said one or more objects, said first image comprising object height information. Said second radiation means is arranged for illuminating at least a portion of the substrate comprising one or more objects, when the substrate is in said object plane, said imaging means thereby generating a second image of at least one of said one or more objects, said second image comprising object area information. Said sensor means comprises extraction means for extracting, from said first image, object height information, and for extracting, from said second image, object area information.

The generation of a first and a second image used for extracting object height information and object area information respectively in combination with employment of a matrix sensor means having a portionwise addressable matrix of pixel elements provides for an efficient and flexible use of the generated image information for inspecting and determining properties of the one or more objects. Characteristic for such a sensor means is the matrix of pixel elements and the possibility to address, and thus read out, only a portion of the whole matrix at a time. Portionwise is to be interpreted as at least one pixel at a time. This possibility is inventively employed to dedicate different combinations of pixel elements for different tasks. By generating two different images, by means of said first and second radiation means, the multitask capability is inventively and efficiently used.

In comparison to the above described device and method of U.S. Pat. No. 5,134,665 the present invention provides for both 2-dimensional and 3-dimensional inspection of objects more or less simultaneously while moving the substrate and the device in relation to each other.

The expression "objects on the substrate" comprise many different possible objects, such as for example adhesive, flux, conductive adhesive, soldered seams, electronic components, soldered electronic components, bumps, pins, and, particularly, deposits such as single or groups of solder paste or adhesive dots. The deposits may also comprise satellites, i.e. unwanted droplets of dispensed solder paste, adhesive, conductive adhesive, etc., from the dispensing process.

By "radiation" is meant different types of light, such as visible light, infrared light, ultraviolet light, etc.; and by "frequency" is meant the frequency of the radiation waves. Instead of "frequency" the term "wavelength" could be equivalently used.

In an advantageous embodiment of the invention the sensor comprises on-chip signal processing capability. The signal processing consequently is performed on the same chip as the pixel elements are formed, which enhances the speed of the device by reducing the amount of output needed to be applied to external processing means.

In an advantageous embodiment of the invention said first and second images are alternatingly processed portion by portion, i.e. the images are processed portionwise and the processing jumps to and fro between the two images. This way of processing is close to parallel processing of the height and area information respectively. By employing a particularly advanced sensor means, in a further embodiment of the invention, it is even possible to perform a true parallel, that is simultaneous, processing of the area and height information respectively.

In yet further embodiments of the invention processing of the first and second images are additionally separated.

One aspect of separation is to separate the generation of the first and second images in time, thereby to minimise a possible difficulty of radiation associated with one of the images interfering with radiation associated with the other image on the sensor in a case where the first and second images overlap on the sensor surface. This time separation rather provides for a use of the same sensor area for sensing both images, which is advantageous in some cases. Additionally, the possibility of illuminating the same area of the substrate without risking radiation interference in the object plane is enhanced.

Another aspect of separation is to separate the first image from the second image by having different, that is geometrically separated, portions of the sensor means illuminated by the first and the second image respectively. As a result the risk of interference is substantially eliminated, and by using, in this way, different sensor elements for the different images the total rate of images generated can be increased.

A further aspect of separation is to separate the first image from the second image by separating the radiation originating from said first and second radiation means in a first and a second range of frequencies respectively, and by at least filtering the radiation impinging a first portion of the sensor means so that radiation within one of said first and second ranges of frequencies is passed and radiation within the other one of said first and second ranges of frequencies is stopped. In addition to the above mentioned advantages of the enhanced separation, this aspect provides for a possibility to at least to some extent limit the area inspected on the substrate by limiting the dimensions of said first portion. Optionally, two or more portions of the sensor means are covered by filters passing radiation within different frequency ranges.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF EMBODIMENTS

Figure 1:
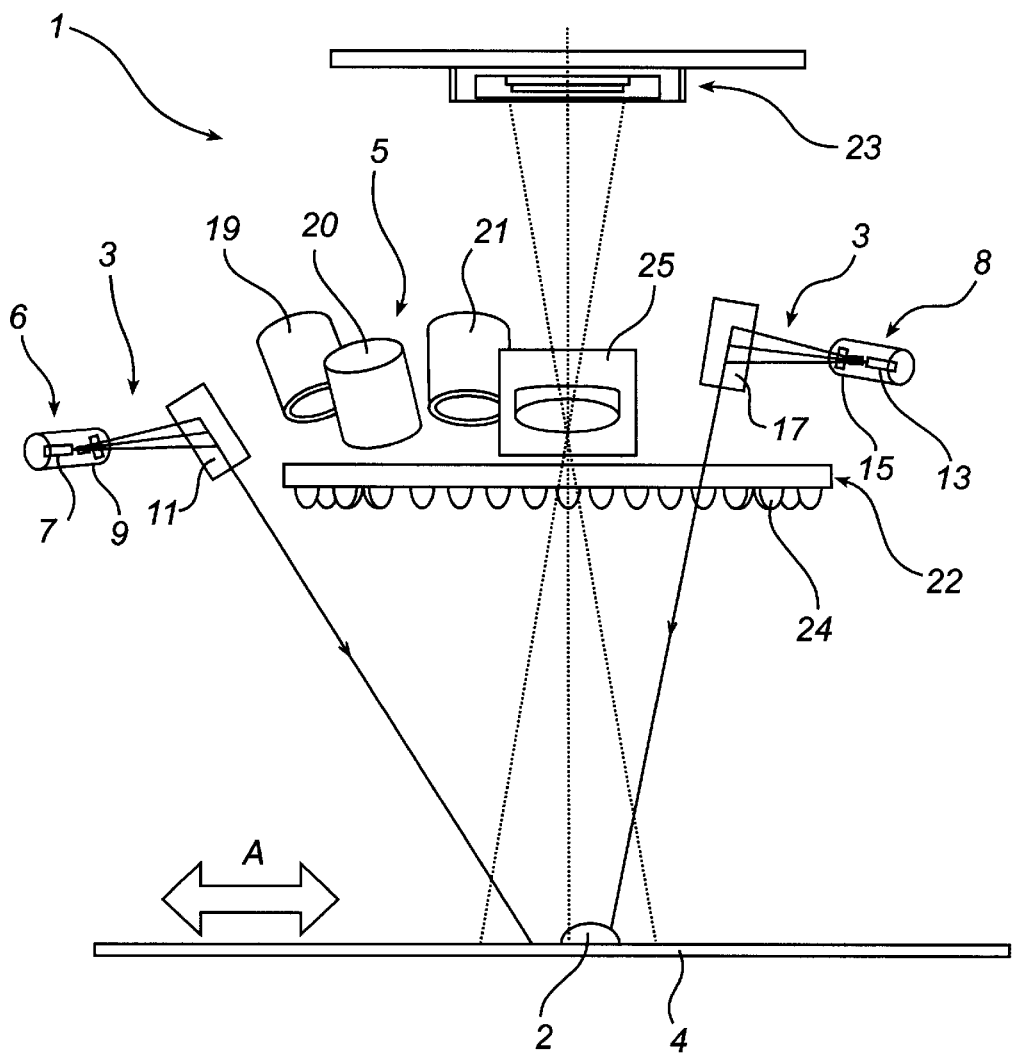
FIG. 1 is a schematic view of a device in accordance with an embodiment of the present invention.

A device according to an embodiment of the present invention is shown in FIG. 1. The device 1 is arranged above a substrate carrying an object 2 to be inspected. The device 1 and the object 2 are moving mutually, i.e. relative to each other, which is indicated by an arrow A. The object 2 could be of many different kinds as mentioned above. However, for the sake of simplicity of explanation, let us in the following assume that the object 2 is a solder paste deposit, which has been dispensed on the surface of the substrate, designated by 4. Generally, the inspected object 2 covered by the illuminated inspection area embraces a deposit comprising several dots but for reasons of clarity only a single dot 2 is shown in the drawings.

The device 1 comprises a first radiation means 3 for generating radiation of a first range of frequencies, or wavelengths, and a second radiation means 5 for generating radiation of a second range of frequencies. In this embodiment the first radiation means 3 comprises two similar radiation generators 6, 8, a first one 6 thereof comprising a first laser source 7, preferably a laser diode, a first optically refractive means 9, preferably a pair of cylindrical lenses, and a first radiation directing means 11; and a second one 8 thereof similarly comprising a second laser source 13, a second optically refractive means 15, and a second radiation directing means 17. The radiation directing means 11, 17, which direct the generated radiation onto the substrate 4, are preferably comprised of flexible and lightweight mirrors, However, several alternatives are possible, such as prisms. The second radiation means 5 comprises a third, a fourth, and a fifth radiation generator 19, 20 and 21 respectively. In the illustrated preferred embodiment each of the third, fourth and fifth radiation generators 19, 20, 21 comprises a LED source, constituted by a set or group of LED (light emitting diode) elements, and refractive optics (not separately shown).

Additionally, the device 1 comprises a third radiation means 22 preferably constituted by a ringshaped radiation generator comprising a plurality of individual LEDs 24 and refractive optics (not separately shown).

The preferred choice of different types of radiation generators will be further explained below.

Figure 7:
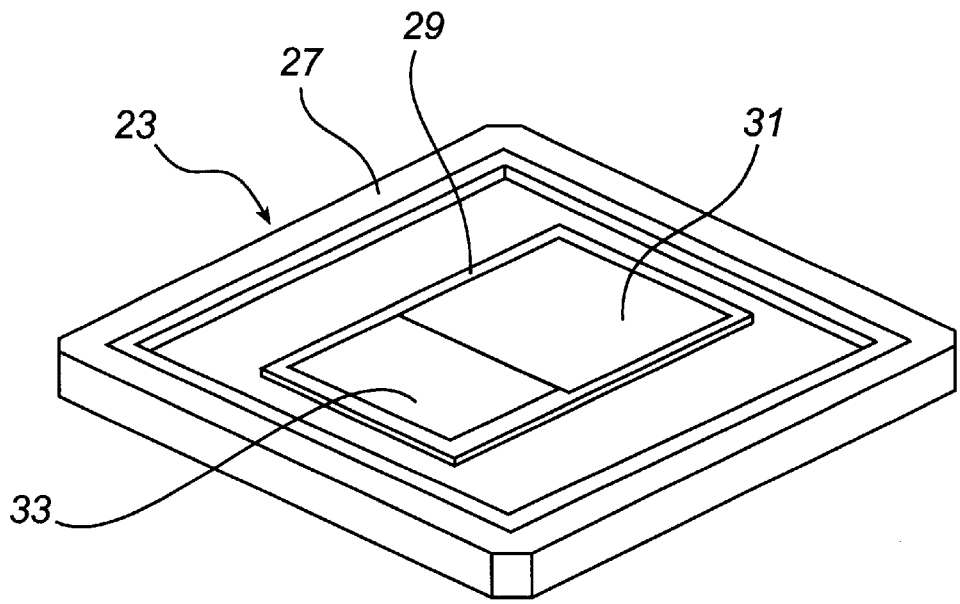
FIG. 7 is a schematic perspective view of the sensor means, illustrating the construction thereof.
Figure 8:
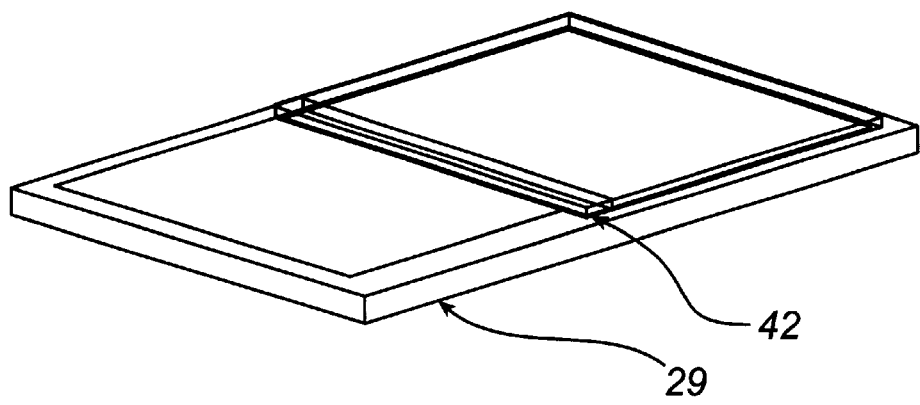
FIG. 8 is a schematic perspective view of an enlarged detail of the sensor means of FIG. 7.

The device 1 further comprises sensor means or simply a sensor 23, arranged for detecting an image of the object 2 and imaging means 25 for creating said image by imaging the object 2 onto the sensor 23. Preferably, the sensor 23 is a two-dimensional matrix sensor having on-chip signal processing capability. As is shown in FIGS. 7 and 8 the sensor 23 comprises a support 27 and an integrated circuit or chip 29 supported by the support 27. The chip 29 carries two parts 31, 33, a first one thereof constituting a radiation sensitive unit 31 and a second one thereof constituting a set of processing units 33, as also shown in FIG. 4b.

Figure 2:
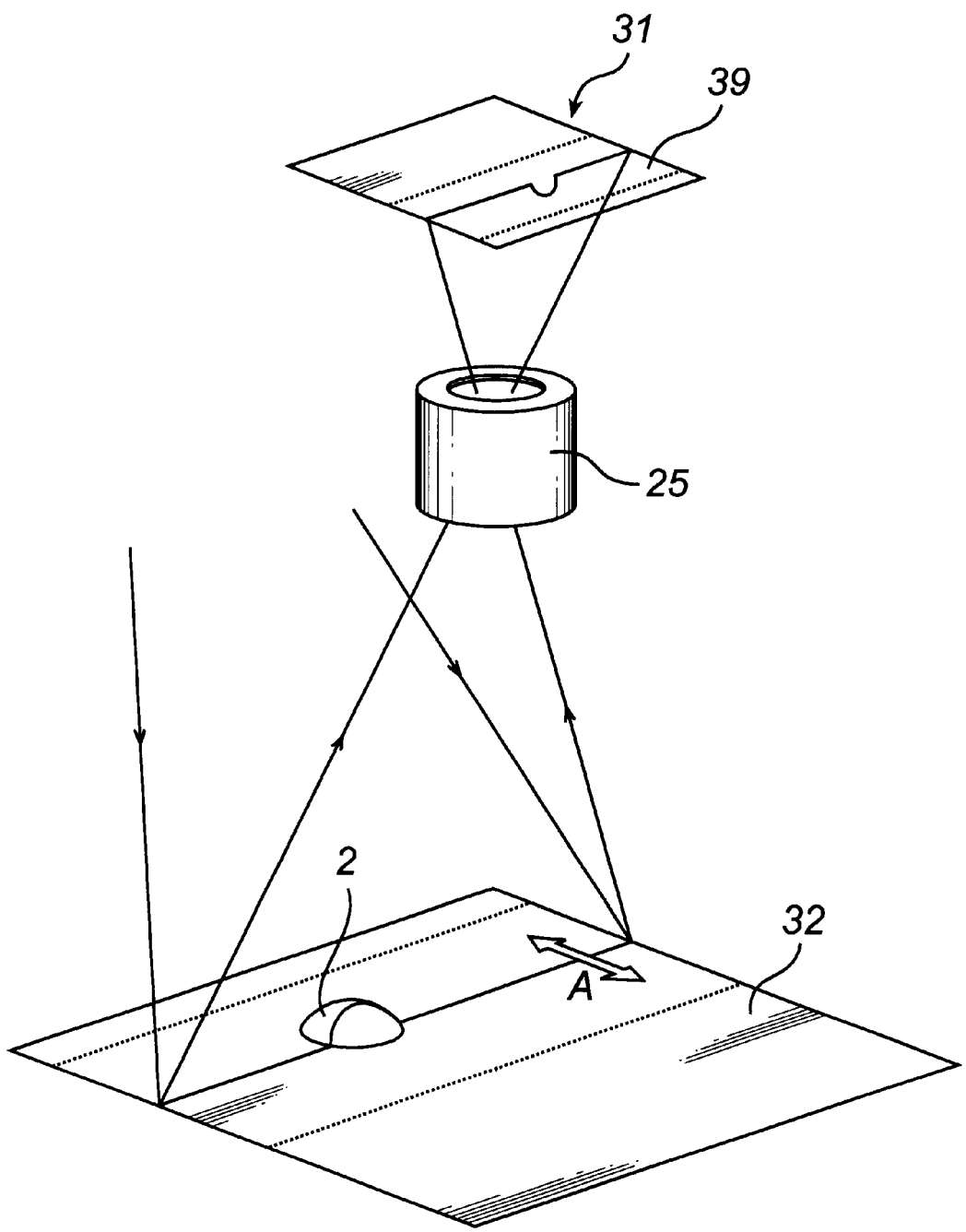
FIG. 2 is a schematic view of a range imaging technique employed by the device in FIG. 1.
Figure 3:
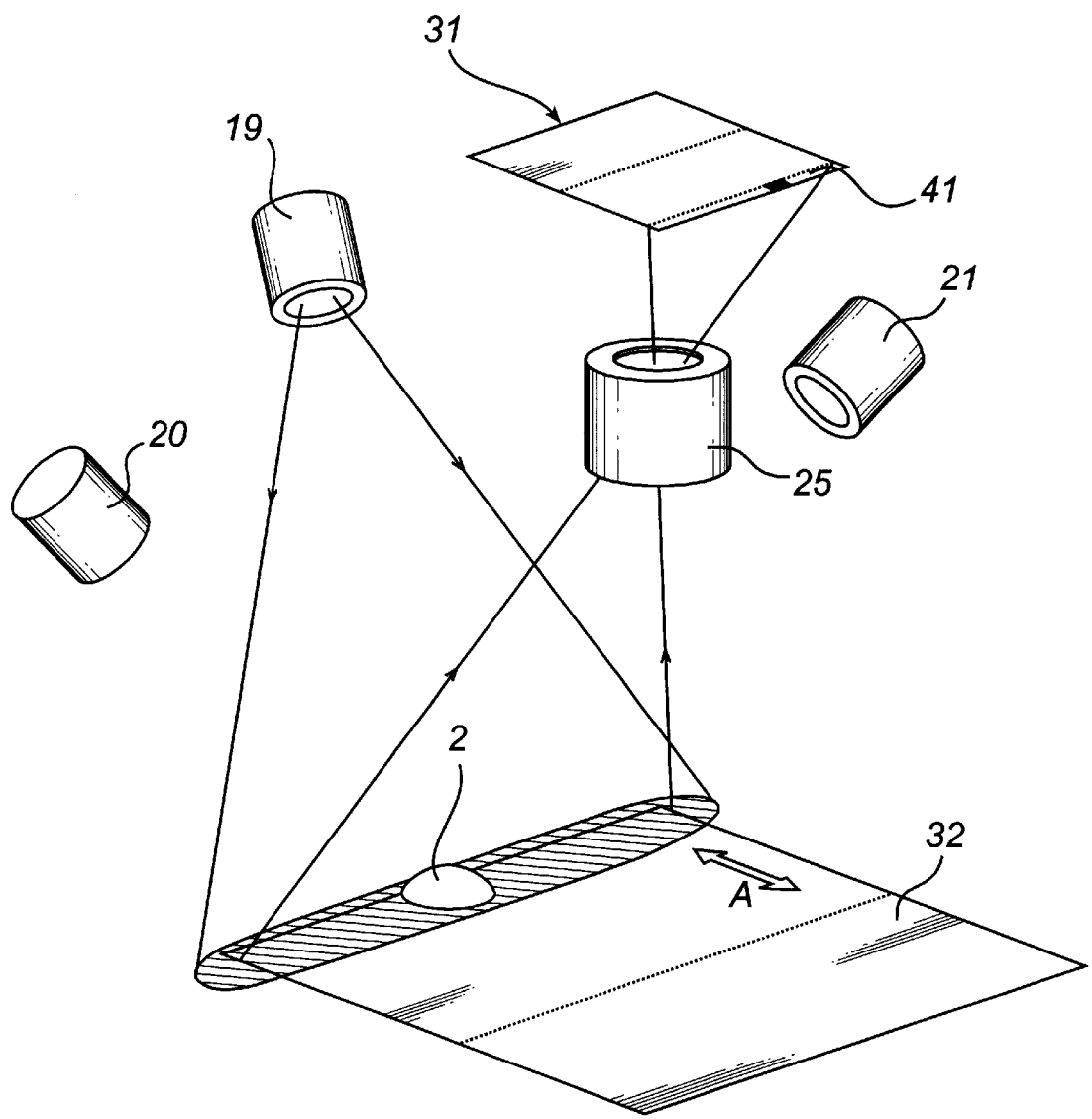
FIG. 3 is a schematic view of a line scan technique employed by the device in FIG. 1.

In this embodiment, said imaging means 25 is constituted by refractive optics, i.e. a lens system. The lens system 25 is arranged to optically forward radiation originating from the object 2 to the sensor 23. In other words, the lens system 25 is arranged to image an object plane 32, as shown in FIGS. 2 and 3, onto an image plane. The radiation originated from the object 2 is originally generated by the radiation generators 6, 8, 19, 20, 21, 22 and reflected or reemitted by the object 2.

The radiation generators 6 and 8 are arranged at a distance from each other illuminating the object 2 from different, preferably opposite, directions and, in this embodiment, as shown in FIG. 1, at different angles of incidence, i.e. angles to the object plane 32, There are at least three important properties associated with the choice of the angles of incidence. They are occlusion, vertical resolution and dynamic range of vertical measurement. By choosing different angles it is possible to choose a different resolution and a different dynamic range for the inspection of different objects. Unfortunately, there will be some occlusion problems. On the other hand, if the angles are chosen to be equal, which is an alternative embodiment, occlusion is substantially avoided, while on the other hand the resolution and dynamic range are fixed.

The third, fourth and fifth radiation generators 19–21 are arranged at a distance from each other illuminating the object 2 from different directions and preferably at different angles to the object plane 32. However, these radiation generators illuminate the same area of the object 2.

The third radiation means 22 is among other things used for providing an even illumination of the whole substrate surface area imaged on the radiation sensitive unit 31. It provides an enhanced contrast between surfaces of the objects that are to be inspected and the closest background. Further, the third radiation means 22 is used for illuminating fiducials or reference markers on the substrate 4 for enabling aligning of the substrate to the inspection device 1, and for calibrating the optics.

Figure 4A:
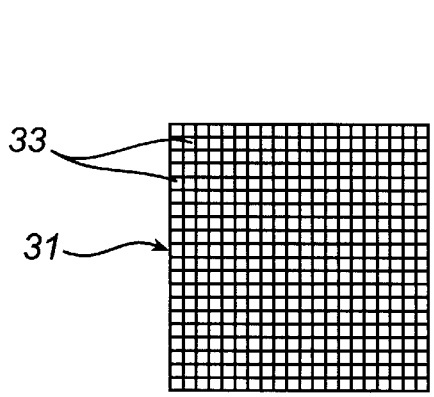
FIG. 4a–b are schematic views of the radiation sensitive surface of a sensor means comprised in the device of FIG. 1.
Figure 4B:
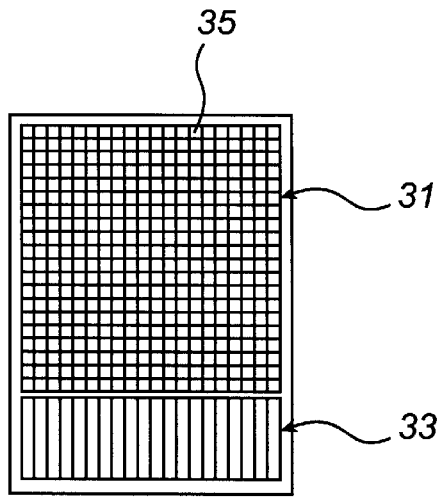

As shown in FIG. 4a and FIG. 4b, the radiation incident on the sensor 23, and more particularly on the radiation sensitive unit 31, is sensed by radiation sensing elements or pixels 35 arranged in a matrix on the surface of the radiation sensitive unit 31. The pixels 35 are, at least a subset thereof at a time, connectable to the set of processing units 33, where each processing unit 33 handles a single pixel 35. For example, in the sensor called MAPP2200 and manufactured by IVP, all pixels in one row at a time are handled in parallel by an array of processing units. Which row to be analysed is optional.

As another example, in a so-called APS, short for active pixel sensor, all pixel elements are individually addressable. The APS is also a matrix sensor where pixels are arranged on a chip. Some means for signal processing of the pixel output signals are integrated on-chip. A DSP (digital signal processor) is used for further processing of the output pixel signals. In a preferred embodiment of the APS, also the DSP is integrated on-chip. Typically, both sensor types are manufactured by means of Complementary Metal Oxide Semiconductor (CMOS) technology, though other methods of manufacture are optionally usable.

Each pixel element converts incident radiation into an electronic-charge, which is then processed by on-chip hardware. Thus, the value of the charge is digitised, either by thresholding or by A/D-conversion.

Further, the on-chip hardware of the sensor 23, at least when it is of the MAPP2200 type, is capable of handling additional tasks necessary to perform in order to obtain useful image information. These tasks include data reduction and template matching or filtering operations which reduce noise or enhance object edges.

The sensor capabilities are inventively employed by the present device. Image information required for determining different properties of the object 2 is either area related information or height related information or both. The sensor 23, or more particularly the radiation sensitive unit 31, is dividable into different subareas each comprising a number of pixels, preferably one or more rows of pixels. The different subareas are dedicated for extraction of either area related or height related image information.

Figure 5:
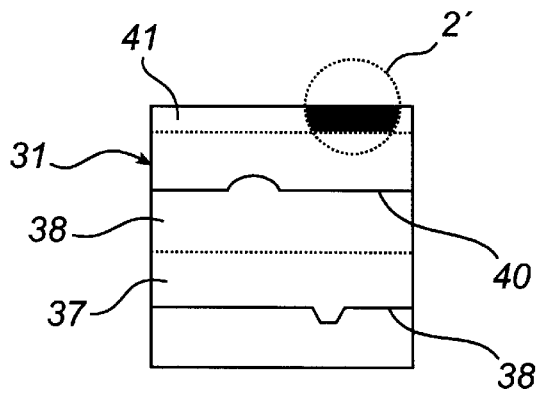
FIG. 5 illustrates division of the radiation sensitive surface of the sensor means of FIG. 4 into subareas.
Figure 6:
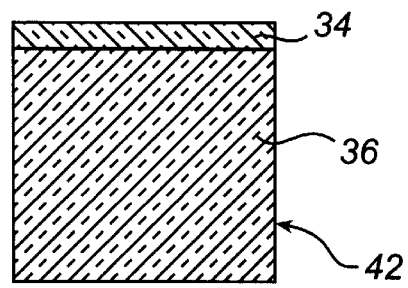
FIG. 6 illustrates a filter means divided into subareas.

In this preferred embodiment the radiation sensitive unit 31 is divided into first and second subareas 37, 39 for extracting height information and a third subarea 41 for extracting area information, as shown in FIG. 5. For reasons to be described below the division of the radiation sensitive unit 31 is preferably done physically as is shown in FIG. 6. A filter means or filter layer 42 is arranged on the surface of the radiation sensitive unit 31. The filter means 42 is provided with a first narrow all pass portion 34, and a second portion 36 passing said first range of frequencies radiated from the first radiation means 3, and stopping said second range of frequencies, radiated from the second radiation means 5. Consequently, for a full use of this filter means 42 the first and second frequency ranges are spaced apart, i.e. one of the separation aspects mentioned above in the summary of the invention is employed in this embodiment, which is to be further discussed below.

The first and second radiation means 3, 5 are adapted for providing the sensor 23 with first and second images respectively, the first image being generated so as to substantially comprise height information and the second image being generated so as to substantially comprise area information. In order to obtain these different images, on one hand the radiation generated by said first means 3 is laser radiation of said first frequency range and line, or sheet, shaped when reaching the object plane 32. This is also called sheet-of-light illumination. On the other hand, the radiation generated by said second radiation means 5 is LED radiation having a less limited shape when reaching the object plane 32. The sheet-of-light illumination is illustrated in FIG. 2, and the LED illumination is illustrated in FIG. 3. For sake of clarity, in both figures, the radiation of a single generator is shown.

The first and second radiation generators 6, 8 are arranged so as to illuminate a first portion of the substrate 4 and the third to fifth radiation generators 19, 20 and 21 are arranged so as to illuminate a second portion of the substrate 4. The reason for separating the illuminated first and second portions is to prevent radiation interference negatively affecting the extraction of height information and area information respectively. However, alternative embodiments, such as the one providing a time separation as mentioned above, enable illumination of the same portions. The separation is enhanced by separating the first and second frequency ranges in frequency combined with using the filter 42, while alternative embodiments employ overlapping frequency ranges.

The choice of different types of radiation generators 6, 8 and 19–21 respectively is dependent on the construction of the sensor 23, the division of the radiation sensitive unit 31 and the different types of image information extracted. Since the height of the object is determined by triangulation, height profiles of the object 2 are generated by means of the sensor 23, requiring the used subareas 37, 39 to be large enough, typically several adjacent pixel rows are employed, to encompass such profiles. Each sheet-of-light generates one profile. Consequently, as shown in FIG. 5, in this embodiment two profiles 3B and 40 respectively are generated. As is illustrated, since the illuminated areas on the substrate 4 are different for the first and second radiation generator 6 and 8 respectively, the profiles 38, 40 are associated with different objects or different portions of a single object. Typically, a few profiles per object 2 are enough to obtain sufficient height information, in combination with the area information, to be able to determine requested properties.

The area information is achieved by line scanning, which means that the object 2 is scanned line by line, the lines being adjacent. Typically, one line corresponds to a single pixel row on the radiation sensitive unit 31, all pixels of the row being processed in parallel. In order to achieve such a thin line of radiation incident on the sensitive unit 31 it would be natural to illuminate the object in a correspondingly narrow area using a laser source. However, this has proven difficult due to speckle noise induced by local interference in the object 2. The problem of speckle noise is eliminated by using non-coherent radiation such as that generated by the LEDs, which accordingly is preferred. On the other hand, when using LEDs, difficulties may arise in limiting the illuminated area. By rather limiting the subarea 41 used for receiving area information on the sensor 23 to, for example, a single row of pixels the later problem is avoided. Still, however, the area in the object plane 32 illuminated by the LED sources of the third to fifth radiation generators 19–21 is limited by means of refractive optics in order to separate it from the areas illuminated by the laser sources 7, 13 of the first and second radiation generators 6 and 8 respectively. A further object of limiting the area by means of the refractive optics is to achieve a higher intensity of the radiation within the illuminated area of the substrate 4. The above described spectral filter is preferably employed for enhancing the separation.

For obtaining the height information, it is possible to achieve a good resolution even if the width of the sheet-of-light or laser line amounts to a few rows of pixels, such as 3–5 rows. Thereby the impact of the speckle noise is substantially decreased, which enables the use of the laser sources 7, 13.

Further, each of the first and second radiation generators 6, 8 generates an individual laser line which is imaged on a separate portion of the radiation sensitive unit, i.e. the first and second subareas 37, 39 respectively, as is shown in FIG. 5. Consequently, different resolutions, i.e. number of pixel rows, may be employed.

Thus, while moving the object 2 in relation to the device 1 the row of pixels forming the subarea 41 is consecutively sampled and processed for extracting object area information line by line. This processing is combined with processing of the height information collected by correspondingly sampling the rows of pixels of the other subareas 37, 39. Preferably, the area information and the height information are alternatingly extracted in order to use the full capacity of the sensor. The alternating determinations are principally run in parallel by chopping the jobs, thus executing alternatingly portions of a whole line and area respectively. Thereby, a high speed of movement is enabled while keeping the accuracy at a high level.

In order to enhance the results at a high speed movement the radiation generators 6, 8, 19, 20, 21 are preferably pulsed, or the radiation emitted is pulsed, thereby to minimise blurring caused by the movement while the radiation generators are emitting radiation.

As is evident from the above, the sensor 23 generates digital output signals. These output signals are communicated to a control means, such as a CPU (central processing unit) (not shown), further processing said output signals. The output signals comprise height information output and area information output used by the control means to determine different properties of the object 2. Further, the control means is used by a user to program the sensor 23. The programming may comprise for example defining the different subareas 37, 39, 41 and initiating different image processing capabilities thereof such as those sharpening object edges. Due to the on-chip hardwired and/or programmed signal processing capabilities of the sensor 23, the amounts of data exchanged between the sensor 23 and the control means are reduced, enabling a faster object inspection process. When using an advanced sensor such as MAPP2200 the on-chip capabilities are complex enough to assert that the signal processing performed on-chip is an image processing.

The present invention is provided for inspecting objects on a substrate, and particularly solder paste deposits 2 dispensed thereon, A substrate arranged for surface mounting components is provided with printed platforms or pads for receipt of component connection terminals. The components are connected to the pads by soldering. The solder paste is pre-applied to the pads by some general method, like screen printing or dispensing. In order for the subsequent mounting and soldering of the components to be successful it is important that the solder paste deposit, below simply referred to as deposit, is correctly shaped and positioned, and that no solder paste satellites are generated.

Due to the small dimensions of the deposit, typically in the order of fractions of a millimetre, accurate measurements of high resolution is required of the inspection device. Due to quality requirements it is desired that every deposit on a substrate is inspected after being dispensed. Further, the dispensing rate is high and continuously increasing and consequently it is desired to be able to perform the inspection at a high rate as well. Additionally, it is desired to be able to determine different properties, such as those mentioned above.

By the present invention a high rate is enabled by the inventive use of the sensor 23. As to the different properties desired to determine, the area information is obtained line by line as described. The above mentioned MAPP2200 sensor is able to generate adjacent area lines corrected for occasional erroneous pixels and having distinct limits between the deposit and the surrounding pad or pads. The lines are output to the CPU which calculates the very area of the deposit, Similarly, a number of height profiles also pre-processed on-chip, or, alternatively, in another way either internal or external of the device 1, are output to the CPU. The area and height outputs are position associated by the sensor, and thereby the CPU is able to combine the height and area information related to the same deposit for determining volume etc. A future even more advanced sensor will most likely be able to perform many further calculations on-chip and it is likely to believe that the sensor will contain one processing unit per pixel instead of a number of processing units corresponding to the number of pixels in a row.

The device 1 adapts the illumination, by adapting the emitted radiation of the radiation generators 6, 8, 19–22, according to properties of the present objects 2 under inspection in order to facilitate the signal processing and enable a reliable and accurate information extraction. A typical goal of the adaptive illumination is to emphasise the contrast between an object and its neighbouring background. Adaptable parameters are at least the following:

The intensity of the radiation is tuned in order to obtain high enough levels of contrast.

The angle of incidence towards the objects is usable in order to emphasise the contrasts.

The polarisation of the radiation is efficiently usable for reducing for example glitter from bright objects. For this purpose one polariser is provided between the radiation generator 6, 8, 19–22 and the substrate 4, or more particularly the object or objects thereon. Additionally, another polariser is provided in front of the sensor 23, the orientation thereof being perpendicular to the first mentioned polariser. As a result all reflections which are direct, i.e. which do not change the polarisation caused by the first polariser, is then blocked by the second polariser. On the other hand, the radiation which is spread in the surface of the object 2 is given a randomised contribution of polarisation and thereby reaches the radiation sensitive unit 31.

The frequency/wavelength of the radiation.

The device of the present invention is implementable as a stand-alone apparatus, or as a part of a machine for dispensing solder paste, screen printing, mounting components, etc.

Above some embodiments of the present invention has been described. These should be seen as merely non-limiting examples. Many additional modifications will be possible within the scope of the invention as defined by the claims.

What is claimed is:

1. A method for contactless inspection of objects on a substrate, by means of an inspection device during relative motion between the substrate and the inspection device, said method comprising the steps of:

generating a first image comprising object height information by illuminating at least a portion of the substrate comprising one or more objects by means of first radiation means and imaging at least one of said one or more objects illuminated by said first radiation means onto a two-dimensional matrix sensor means having a portionwise addressable matrix of pixel elements;

generating a second image comprising object area information by illuminating at least a portion of the substrate comprising one or more objects by means of second radiation means and imaging at least one of said one or more objects illuminated by said second radiation means onto said sensor means;

extracting the object height information, by means of said sensor means, from said first image; and extracting the object area information, by means of said sensor means, from said second image.

2. A method according to claim 1, wherein the step of generating a first image is separated in time from the step of generating a second image.

3. A method according to claim 1, further comprising the step of separating the first image from the second image by imaging the first and second images respectively onto separate portions of said sensor means.

4. A method according to claim 1, further comprising the step of separating the first image from the second image by illuminating different portions of the substrate with said first and second radiation means respectively.

5. A method according to claim 1, further comprising the step of separating the first image from the second image by separating the radiation originating from said first and second radiation means in a first and a second range of frequencies respectively, and by filtering at least the radiation impinging a first portion of the sensor means so that radiation within one of said first and second ranges of frequencies is passed and radiation within the other one of said first and second ranges of frequencies is stopped.

6. A method according to claim 1, further comprising the step of using said area and height information for calculating object volume.

7. A method according to claim 1, further comprising the step of using said area information for calculating object position.

8. A method according to claim 1, further comprising the step of using said area information for calculating shape of object outline.

9. A method according to claim 1, further comprising the step of using said area information for calculating object diameter.

10. A method according to claim 1, wherein at least some signal processing is performed on-chip.

11. A method according to claim 10, further comprising the step of performing said area and height information extractions on-chip.

12. A method according to claim 1, further comprising the step of alternatingly processing said first and said second image for obtaining said height and area information respectively.

13. A method according to claim 1, further comprising the step of processing said first and said second image in parallel for obtaining said height and area information respectively.

14. A method according to claim 1, wherein the substrate is illuminated by said first radiation means in the form of a sheet-of-light illumination.

15. A method according to claim 1, wherein said step of extracting area information is performed by line scanning.

16. A method according to claim 1, wherein said step of extracting height information is performed by triangulation.

17. A method according to claim 1, further comprising the step of tuning, adaptively, at least one of said first and second radiation means in response to changing conditions.

18. A device for inspecting objects on a substrate during relative motion between the substrate and the inspection device, comprising:
- a two-dimensional matrix sensor means having a portion-wise addressable matrix of pixel elements;
- a first radiation means;
- a second radiation means; and
- imaging means for imaging radiation originating from an object plane onto the sensor means;
- said first radiation means being arranged for illuminating at least a portion of the substrate comprising one or more objects, when the substrate is in said object plane, said imaging means thereby generating a first image of at least one of said one or more objects, said first image comprising object height information;
- said second radiation means being arranged for illuminating at least a portion of the substrate comprising one or more objects, when the substrate is in said object plane, said imaging means thereby generating a second image of at least one of said one or more objects, said second image comprising object area information;
- said sensor means comprising extraction means for extracting, from said first image, object height information, and for extracting, from said second image, object area information.

19. A device according to claim 18, wherein the sensor comprises on-chip signal processing capability.

20. A device according to claim 19, wherein said on-chip signal processing capability is provided by at least said extraction means.

21. A device according to claim 20, wherein said on-chip signal processing capability is further provided by on-chip means for calculating one or more object properties by means of at least either of said object height information and said object area information.

22. A device according to claim 18, wherein the generation of the first image is separated in time from the generation of the second image.

23. A device according to claim 18, wherein the sensor is provided with at least a first portion for receiving the first image and a second portion, separate from the first portion, for receiving the second image.

24. A device according to claim 18, wherein the first radiation means is provided for generating radiation within a first range of frequencies, wherein the second radiation means is provided for generating radiation within a second range of frequencies, and wherein the device further comprises at least a first filter means passing radiation within one of said first and second ranges of frequencies and stopping radiation within the other one of said first and second ranges of frequencies, said filter means covering a first portion of said sensor means.

25. A device according to claim 18, said device being arranged for extracting the object area information by means of line scanning.

26. A device according to claim 18, said first radiation means comprising a laser generating the radiation by way of a sheet-of-light.

27. A device according to claim 18, said radiation means comprising light emitting diodes (LEDs).

28. A device according to claim 18, wherein each pixel element is individually addressable.

29. A device according to claim 18, wherein at least one of said radiation means is adaptively tuneable.

30. A device according to claim 18, further comprising a third radiation means for illuminating an area of the substrate corresponding to the whole matrix of pixel elements.

31. A device according to claim 30, wherein at least one of said first, second and third radiation means is provided with a first polariser and wherein at least a part of the sensor is provided with a second polariser arranged perpendicular to the first polariser.

32. A device according to claim 25, said first radiation means comprising a laser generating the radiation by way of a sheet-of-light.

33. A device according to claim 32, wherein the first radiation means is provided for generating radiation within a first range of frequencies, wherein the second radiation means is provided for generating radiation within a second range of frequencies, and wherein the device further comprises at least a first filter means passing radiation within one of said first and second ranges of frequencies and stopping radiation within the other one of said first and second ranges of frequencies, said filter means covering a first portion of said sensor means.

34. A device for inspecting objects on a substrate during relative motion between the substrate and the inspection device, comprising:
- a two-dimensional matrix sensor having a portionwise addressable matrix of pixel elements;
- a first radiation means;
- a second radiation means; and
- imaging means for imaging radiation originating from an object plane onto the sensor means;
- said imaging means being arranged to generate a first image comprising object height information of an object provided on said substrate and illuminated by said first radiation means, and to generate a second image comprising object area information of an object provided on said substrate and illuminated by said second radiation means, said object height information and said object area information, respectively, being extractable by means of said sensor.

35. A device for inspecting objects on a substrate during relative motion between the substrate and the inspection device, comprising:

a two-dimensional matrix sensor having a portionwise addressable matrix of pixel elements;

a first radiation device;

a second radiation device; and an imaging device arranged to image radiation originating from an object plane onto the matrix sensor;

wherein said first radiation device is arranged to illuminate at least a portion of the substrate comprising one or more objects, when the substrate is in said object plane, wherein said imaging device is arranged to thereby generate a first image of at least one of said one or more objects, said first image comprising object height information;

wherein said second radiation device is arranged to illuminate at least a portion of the substrate comprising one or more objects, when the substrate is in said object plane, wherein said imaging device is arranged to thereby generate a second image of at least one of said one or more objects, said second image comprising object area information;

said matrix sensor comprising an extraction device, which is arranged to extract, from said first image, object height information, and to extract, from said second image, object area information.

* * * * *